(12) United States Patent
Chang et al.

(10) Patent No.: US 10,258,308 B2
(45) Date of Patent: Apr. 16, 2019

(54) ULTRASOUND IMAGE-CAPTURING DEVICE FOR WHOLE BREAST

(71) Applicant: EPISONICA CORPORATION, Hsinchu (TW)

(72) Inventors: Tsun-Ming Chang, Hsinchu (TW); Ihyuan Kuo, Hsinchu (TW)

(73) Assignee: EPISONICA CORPORATION, Hsinchu (TW)

( * ) Notice: Subject to any disclaimer, the term of this patent is extended or adjusted under 35 U.S.C. 154(b) by 276 days.

(21) Appl. No.: 15/291,431

(22) Filed: Oct. 12, 2016

(65) Prior Publication Data

US 2017/0273660 A1  Sep. 28, 2017

(30) Foreign Application Priority Data

Mar. 24, 2016 (TW) .............................. 105204115 U (51) Int. Cl.
 A61B 8/00 (2006.01)
 A61B 8/08 (2006.01)
 A61B 8/14 (2006.01)

(52) U.S. Cl.
 CPC .............. *A61B 8/0825* (2013.01); *A61B 8/14* (2013.01); *A61B 8/406* (2013.01); *A61B 8/42* (2013.01); *A61B 8/4281* (2013.01); *A61B 8/4461* (2013.01)

(58) Field of Classification Search
 CPC ................................ A61B 8/0825; A61B 8/14
 See application file for complete search history.

(56) References Cited

U.S. PATENT DOCUMENTS

| | | | | |
|---|---|---|---|---|
| 4,545,385 | A * | 10/1985 | Pirschel ............... | A61B 8/0825 128/915 |
| 6,459,925 | B1 * | 10/2002 | Nields .................. | A61B 6/0435 128/915 |
| 2004/0102707 | A1 * | 5/2004 | Murkin ................ | A61B 8/4281 600/459 |
| 2005/0143638 | A1 * | 6/2005 | Johnson ............... | A61B 5/4312 600/407 |

* cited by examiner

*Primary Examiner* — Joel F Brutus
(74) *Attorney, Agent, or Firm* — Locke Lord LLP; Tim Tingkang Xia, Esq.

(57) ABSTRACT

A whole breast ultrasound image-capturing device comprises: a platform comprising an opening formed thereon; a mechanical driving system mounted in the opening and comprising a frame mounted on the mechanical driving system, a rotary module comprising a first gear, a second gear engaged with the first gear, and a drive motor connected to the first gear, and a radial movement drive comprising a translation mechanism radially movable; an array probe mounted in the radial movement drive; a holder connected to the translation mechanism to fix the array probe; a gel plate connected to a cam surface of the second gear through connecting frames, mounted on the holder, and comprising a plate opening enclosing the array probe to expose the array probe out of the gel plate; a film assembly mounted in the frame and comprising a film frame mounted in the frame and a film mounted in the film frame.

10 Claims, 9 Drawing Sheets

ULTRASOUND IMAGE-CAPTURING DEVICE FOR WHOLE BREAST

CROSS REFERENCE

This non-provisional application claims priority from Taiwan Patent Application NO. 105204115, filed on Mar. 24, 2016, the entire content thereof is incorporated by reference herein.

FIELD OF THE INVENTION

The present invention is related to an ultrasound image-capturing device for whole breast, and more particularly to a whole breast ultrasound image-capturing device which can provide automatic ultrasound imaging techniques for the whole breast.

BACKGROUND OF THE INVENTION

According to the data from the U.S. Center for Disease Control, breast cancer is one of the commonest cancers in women, and the second leading cause of cancer death in women after lung cancer. Nowadays, breast cancer is the fifth commonest cancer. In 2012, there are approximately 522,000 patients died of breast cancer worldwide. Because of westernized diet, the female population suffered from breast cancer increases worldwide year after year, especially in East Asia. The U.S. Preventive Services Task Force recommends mammography every two years for women at the ages of 50-74.

X-ray mammography has been a common approach in early detection of breast cancer. In this approach, X-ray is emitted to penetrate the breast tissue for image generation. However, X-ray is an ionizing radiation, and therefore its dose for the subject should be in a low dose. Furthermore, the false-negative result from X-ray mammography is due to the difference of breast densities. In addition, the subject feels uncomfortable because the device for X-ray mammography lies on the breast.

In ultrasound detection, no radiation is introduced, and no adverse biological reaction occurs. Therefore, ultrasound detection is a safe way for image generation. After ultrasound is emitted from a probe to a body, it is reflected or scattered back to the probe to be received. The received ultrasound is converted to an electronic signal by a system, and then the image is provided for analysis. The reflected or scattered ultrasound is affected according to physical characteristics of the tissue, e.g. tissue density, and therefore ultrasound can be applied to various kinds of tissues, such as a cyst full of mucus or a solid tissue (a tumor tissue) in the breast. Furthermore, in X-ray mammography, both tissues appear white, but they don't do so in ultrasound detection. As above, breast ultrasound has been used in a supplemental imaging method for detection of high-density breast.

Previously, a handheld ultrasound scanner is employed for screening of breast cancer. This screening greatly depends on a sonographer, and is a labor intensive way for the detection of breast cancer. The scanning consistency varies with different patient workloads, so miss detection happens occasionally.

Accordingly, there is a need to develop a whole breast ultrasound image-capturing device which can provide automatic ultrasound imaging techniques for the whole breast.

SUMMARY OF THE INVENTION

An objective of the present invention is to provide a whole breast ultrasound image-capturing device, and the device can provide automatic ultrasound imaging techniques for the whole breast.

In order to achieve the foregoing and/or other objective(s), the present invention discloses a whole breast ultrasound image-capturing device, the device is configured for breast scanning when a subject lies prone thereon, and the device is associated with an ultrasonic system when used. The whole breast ultrasound image-capturing device comprises: an examination platform, a mechanical driving system, an array probe, a probe holder, a gel plate, and a film assembly.

The examination platform comprises an opening, and the opening is formed on a center of a top portion of the examination platform.

The mechanical driving system is mounted in the opening, and comprises a frame, a rotary module, and a radial movement drive. The frame is mounted on a top portion of the mechanical driving system. The rotary module comprises a first gear, a second gear, and a drive motor, the first gear is engaged with the second gear, and the drive motor is connected to an axis of the first gear. The radial movement drive is mounted on a top portion of the rotary module, and comprises a translation mechanism. The translation mechanism is radially movable.

The array probe is mounted in the radial movement drive.

The probe holder is connected to the translation mechanism to fix the array probe.

The gel plate comprises a bottom portion connected to a cam surface of the second gear through multiple connecting frames, and the gel plate is mounted on a top portion of the probe holder. The gel plate comprises a plate opening, and the plate opening encloses the array probe to expose the array probe out of the gel plate.

The film assembly is mounted in the frame, and the film assembly comprises a film frame and a film. The film frame is mounted in the frame, and the film is mounted in the film frame.

By the foregoing structure, the subject's breasts lean on the film with his/her own weight, and the array probe emits ultrasound from a bottom thereof to penetrate the film so as to scan the breasts.

The device of the present invention can automatically and evenly scan the entire of the subject's breasts. Compared with any prior handheld ultrasound scanner, the device of the present invention has high specificity and high accuracy for breast cancer diagnosis.

DETAILED DESCRIPTION OF THE INVENTION

The detailed description and preferred embodiments of the invention will be set forth in the following content, and provided for people skilled in the art so as to understand the characteristics of the invention.

With reference to FIGS. 1-6, a whole breast ultrasound image-capturing device (1) is present in an embodiment. The device is configured for breast scanning when a subject (3) lies prone thereon, and the device is associated with an ultrasonic system (2) when used. The device comprises: an examination platform (10), a mechanical driving system (11), an array probe (12), a probe holder (13), a gel plate (14), and a film assembly (15).

In one preferable embodiment, the ultrasonic system (2) can outputs a b-mode ultrasound image with high resolution. When high frequency ultrasound formed in a more than 128-channel beamforming system has a frequency ranged from 5 to 13 MHz, a better image is outputted.

The ultrasonic system (2) is, but not limited to, a cart-type ultrasonic system. Furthermore, any commercially available handheld ultrasonic system or any module ultrasonic engine may be used for b-mode ultrasound image generation. Each of the foregoing ultrasonic systems may be positioned in a case under the examination platform (10).

Figure 1:
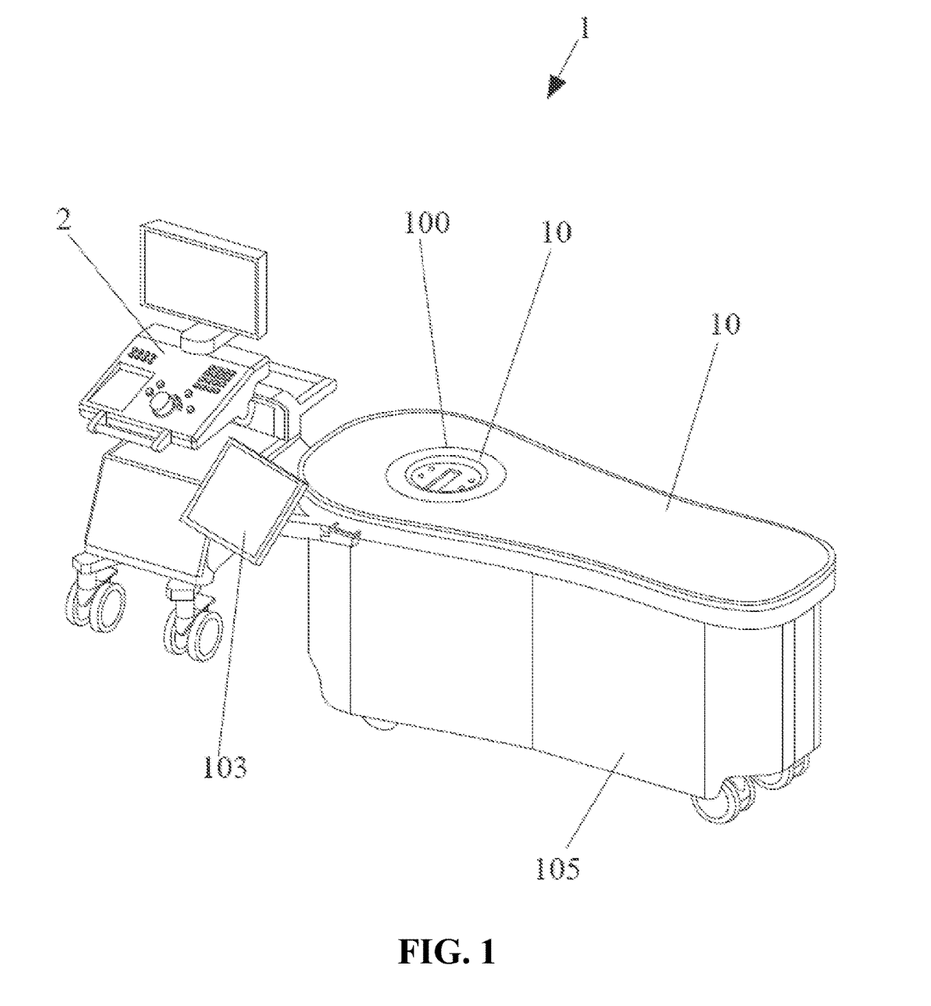
FIG. 1 is a schematic diagram illustrating a whole breast ultrasound image-capturing device according to an embodiment of the present invention.

The examination platform (10) comprises an opening (100). The opening (100) is formed on a center of a top portion of the examination platform (10), and is protected by a tub.

The examination platform (10) is configured for the subject (3) to lie prone thereon for scanning his/her breasts. The examination platform (10) is made of a hard plywood board with a polyurethane foam for cushion and with a smooth synthetic leather for touching with the body. On a bottom portion of the examination platform (10) is mounted a cabinet, a control system (101) and an electronic control element (102) are placed in the cabinet, and other tools for scanning, such as an ultrasound coupling gel and tissue papers, may be placed in the remaining space of the cabinet. A touch panel (103) and the control system (101) are fixed on a side of the top portion of the examination platform (10). The control system (101) is configured with a graphical user interface (GUI) so that the breast scanning can be operated via the touch panel (103). Below the cabinet are mounted four wheels for moving the examination platform (10), and the cabinet is covered with a plastic housing (105).

Figure 3:
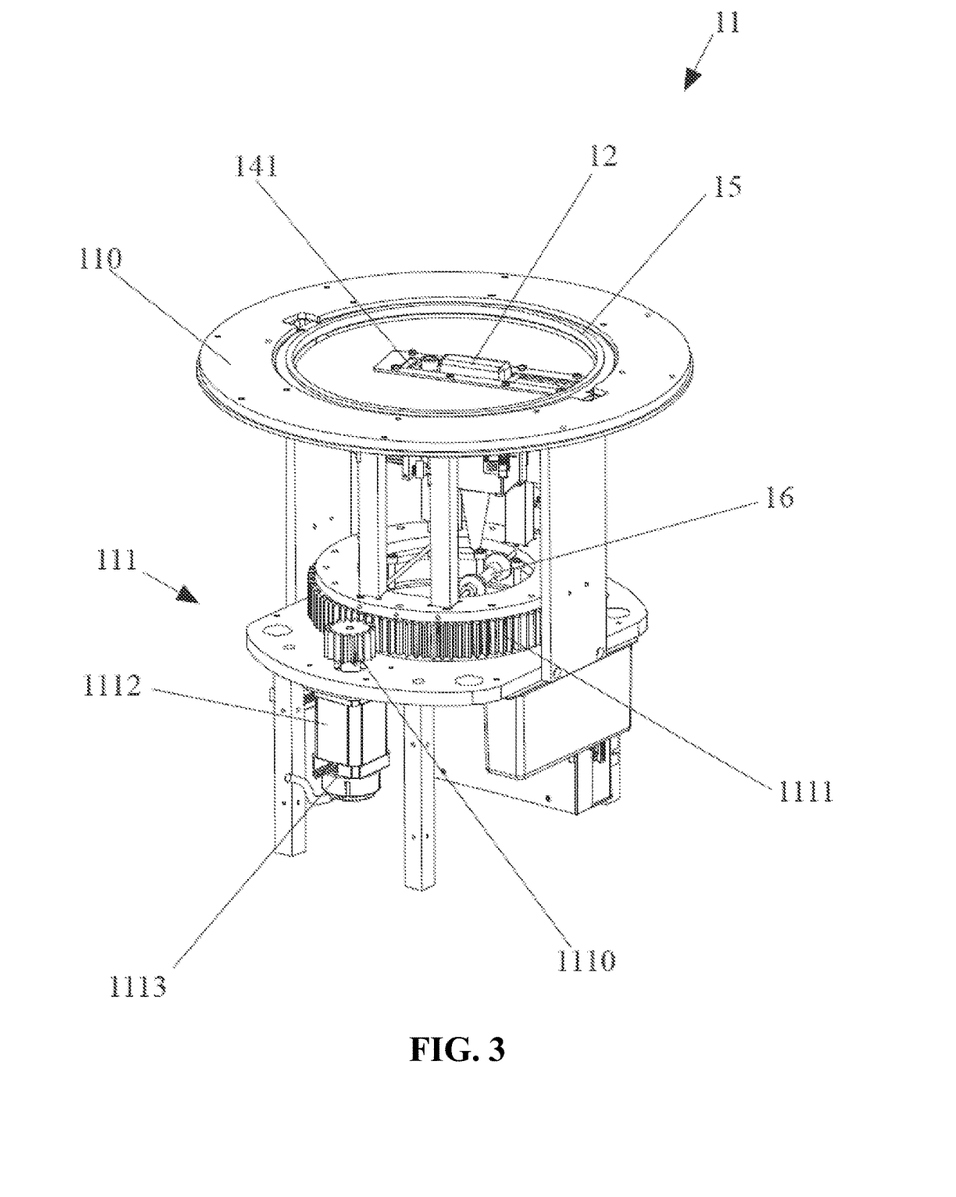
FIG. 3 is a schematic diagram illustrating a mechanical driving system of the embodiment.
Figure 4:
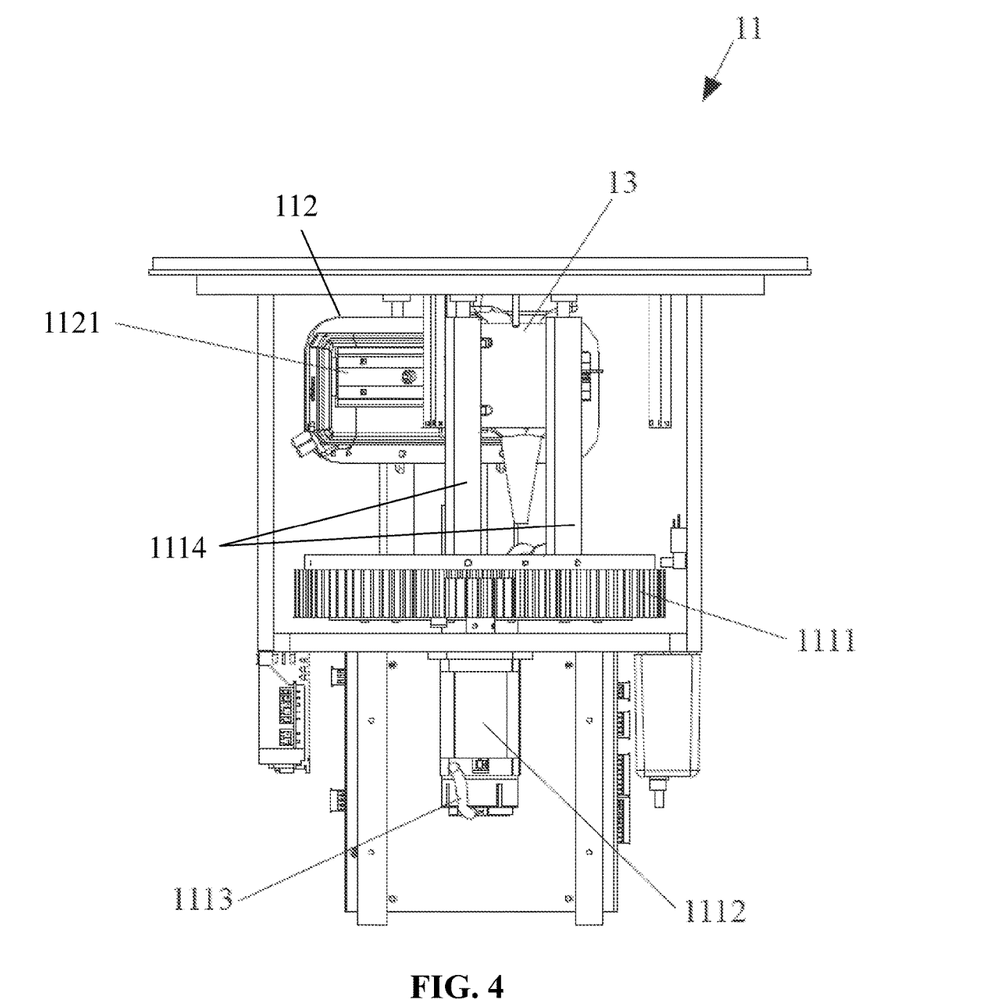
FIG. 4 is a schematic diagram illustrating position of the mechanical driving system shown in FIG. 3.

The mechanical driving system (11) is mounted in the opening, and comprises a frame (110), a rotary module (111), and a radial movement drive (112). The frame (110) is mounted on a top portion of the mechanical driving system (11). The rotary module (111) comprises a first gear (1110), a second gear (1111), and a drive motor (1112). The first gear (1110) is engaged with the second gear (1111), and the drive motor (1112) is connected to an axis of the first gear (1110). In one preferable embodiment, the drive motor (1112) is a step motor.

The radial movement drive (112) is mounted on a top portion of the rotary module (111). The radial movement drive (112) comprises a translation mechanism (1121), and the translation mechanism (1121) is radially movable. In the present embodiment, the rotary module (111) further comprises an encoder (1113), and the encoder (1113) is mounted in back of the drive motor (1112).

The array probe (12) is mounted on the radial movement drive (112), so that the mechanical driving system (11) can drive the array probe (12) to rotate. The array probe (12) is a necessary for b-mode ultrasound image generation, and the footprint size of the array probe (12) is of at least 10 cm.

In one preferable embodiment, the array probe (12) is selected from any of various ultrasound probes having a footprint size of at least 10 cm. As the footprint size is smaller, more radial scanning processes are performed to overlay the whole area of the breasts.

Figure 6:
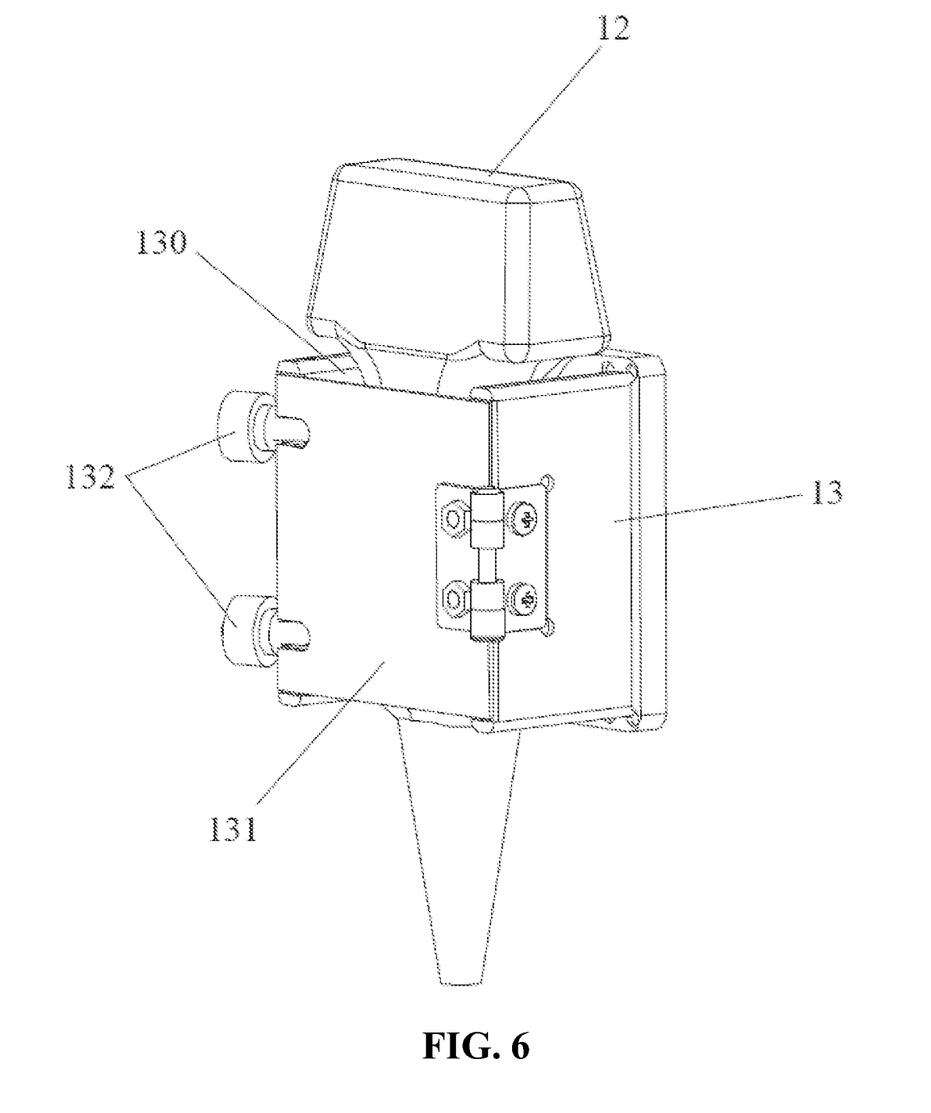
FIG. 6 is a schematic diagram illustrating a probe holder of the embodiment.

The probe holder (13) is connected to the translation mechanism (1121) to fix the array probe (12). Therefore, the mechanical driving system (11) can drive the array probe (12) to radially move between any two predetermined positions for each radial breast scanning process, and to perform multiple radial rotations. Although various probes are commercially available, each of the different probes still can fit in with the probe holder (13).

The probe holder (13) comprises a holder space (130), a movable disk (131), and two screws. The holder space (130) is filled with a plastic crystal material, such as Shapicrystal® or alginate, to match the different types of the array probe (12). The movable disk (131) can be opened with a hinge, and these screws (132) can fix the movable disk (131) so as to allow the array probe (12) to be freely mounted or detached.

Figure 5:
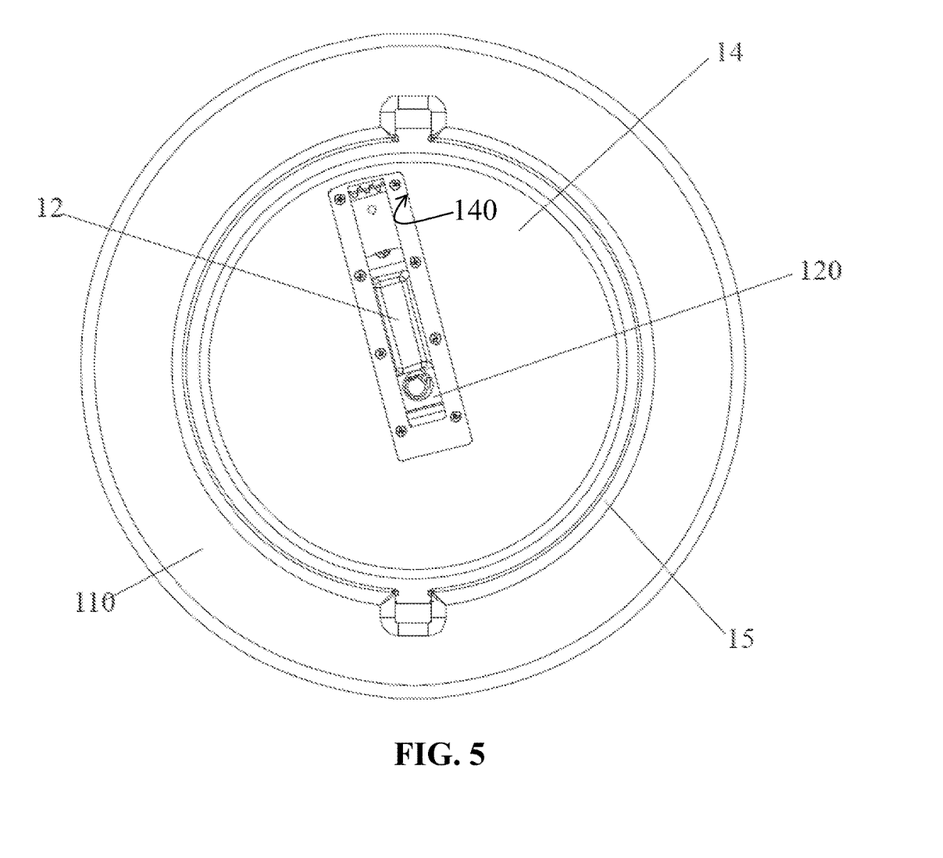
FIG. 5 is a schematic diagram illustrating an array probe of the embodiment faces upward while scanning.

In front of the array probe (12) is mounted a camera (120). In the present embodiment, the whole breast ultrasound image-capturing device (1) further comprises an electric wire collecting device (16). The camera (120) can be used to guide the breasts for image generation. During the scanning, the breasts preferably centrally lie on the mechanical driving system (11). Rotation of the array probe (12) driven by the drive motor (1112), radial movement between any two predetermined positions for each radial breast scanning process, and performance of multiple radial rotations can be controlled by an electronic software.

An electric wire of the array probe (12) and that of the camera (120) can be stored in the electric wire collecting device (16) to prevent these electric wires from twining with each other.

In one preferable embodiment, the camera (20) is a charge-coupled device (CCD) camera or a complementary metal-oxide-semiconductor (CMOS) camera.

The gel plate (14) comprises a bottom portion connected to a cam surface of the second gear (1111) through multiple connecting frames (1114). The gel plate (14) is mounted on a top portion of the probe holder (13), and comprises a plate opening (140) and a cover (141). The plate opening (140) encloses the array probe (12) to make the array probe (12) exposed out of the gel plate and to allow movement of the array probe (12). The cover (141) is stretchable to seal the plate opening (140). By such manner, the gel plate can avoid leaking of the coupling gel as a vacuum bellow. The gel plate (14) can be used as a dripping holder for the coupling gel, and is detachable to allow for easy cleaning.

With reference to FIGS. 2 and 5-7, the film assembly (15) is mounted in the frame (110), and comprises a film frame (150) and a film (151). The film frame (150) is mounted in the frame (110), and the film (151) is mounted in the film frame (150).

Figure 2:
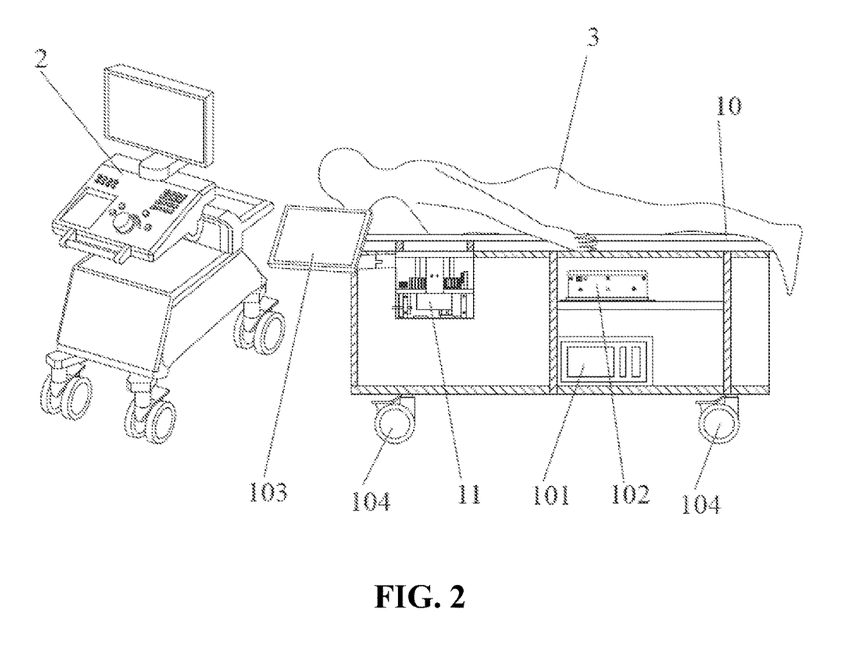
FIG. 2 is a schematic diagram illustrating a subject lies prone on the whole breast ultrasound image-capturing device shown in FIG. 1.

When being scanned, the breasts of the subject (3) lean on the film (151) with his/her own weight. The array probe (12)

emits ultrasound from a bottom thereof to penetrate the film (151) so that the breasts are scanned. In one preferable embodiment, the film (151) is made of a biocompatible material. In another preferable embodiment, the film (151) is made of a material selected from the group comprising polyethylene terephthalate (PET), polyethylene terephthalate glycol-modified (PETG), polyethylene, medical grade polyvinyl chloride (PVC), polycarbonate, polypropylene, polyether ether ketone (PEEK), and polyurethane.

The thickness of the film (151) is selected for required ultrasound transmission, and the ultrasound transmission can be calculated based on the so-called quarter wavelength acoustic impedance matching theory.

Figure 7:
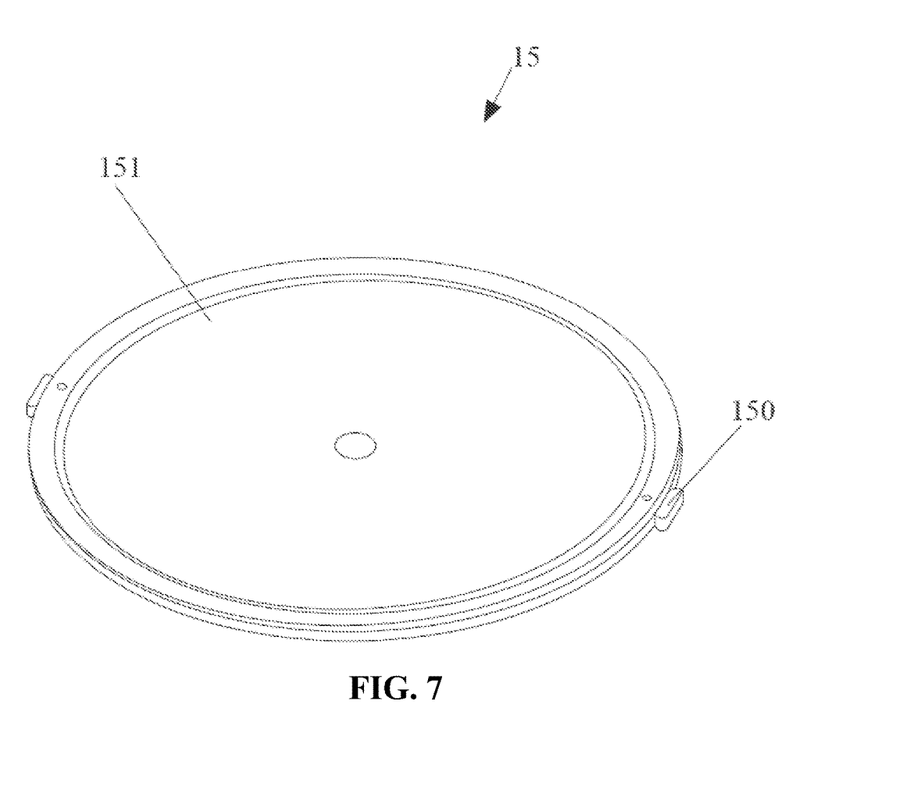
FIG. 7 is a schematic diagram illustrating a film assembly of the embodiment.

When scanning starts, the film assembly (15) rises from the frame (110) to a projecting handle of the film frame (150), and the ultrasound coupling gel is smeared on two surfaces of the film (151) in an amount enough for coupling. A circular mark is formed on a center of the back surface of the film (151). With the subject lying, the circular mark allows the breasts to be aligned with the scan center, and also allows the camera (120) to guide the image for the scanning.

When the radial scanning is performed by the whole breast ultrasound image-capturing device (1) according to the present embodiment, the ultrasonic image can be transferred to and saved in the ultrasonic system (2). Then, the image is transferred to the control system (101) via an internet interface, an USB interface, or an RS232 interface. The command of the control system is sent via any of these interfaces so that the movement of the array probe (12) in the mechanical driving system (11) synchronizes the captured image. In one preferable embodiment, images at different times are transferred to the control system (101) according to the locations of the array probe (12).

In one preferable embodiment, multiple radial scanning processes are needed to overlay the whole area of the breasts, and then the captured images of the same rotation angle are jointed, which can provide easy detection for breast cancer. In order to avoid any negligence in the breast scanning, there is a need to perform an overlap scanning process. In this overlap scanning process, the scan range may be altered. However, the angle in the overlap scanning process is not a key point in the present content, and the angle is selected dependent on user's settings and operational practice.

Figure 8:
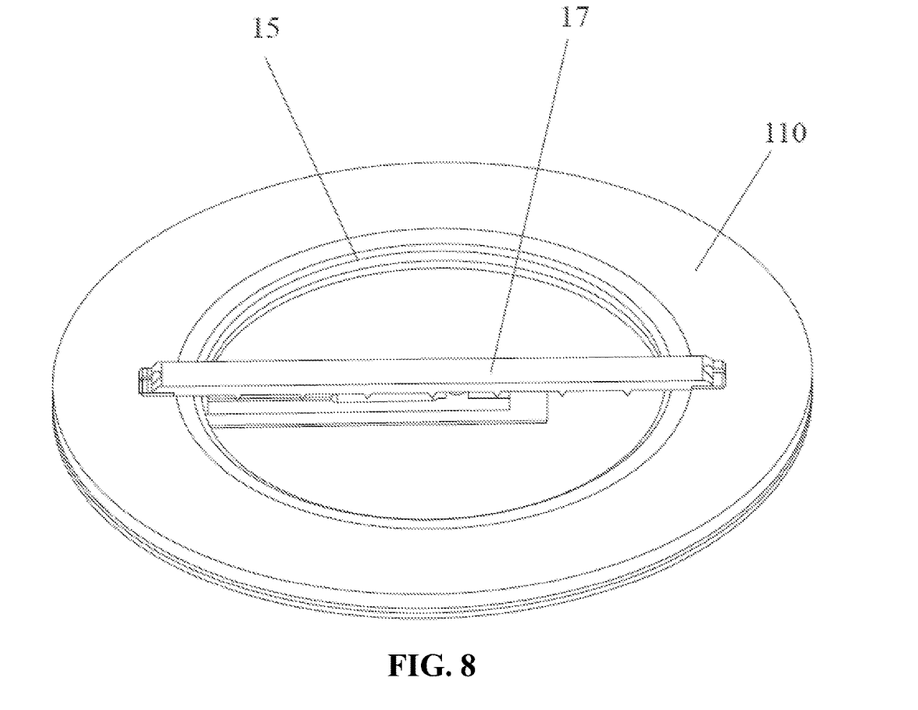
FIG. 8 is a schematic diagram illustrating a datum plate of the embodiment.

As shown in FIG. 8, the whole breast ultrasound image-capturing device (1) further comprises a datum plate (17). The datum plate (17) is connected across two sides of the film assembly (15), and can determine whether the adjacent images captured in the radial breast scanning processes are overlapped or not. The datum plate (17) comprises multiple projections and a slot. In the ultrasonic images, white lines are present as marks. The two adjacent images can be appropriately overlapped by alignment of these white lines.

Figure 9:
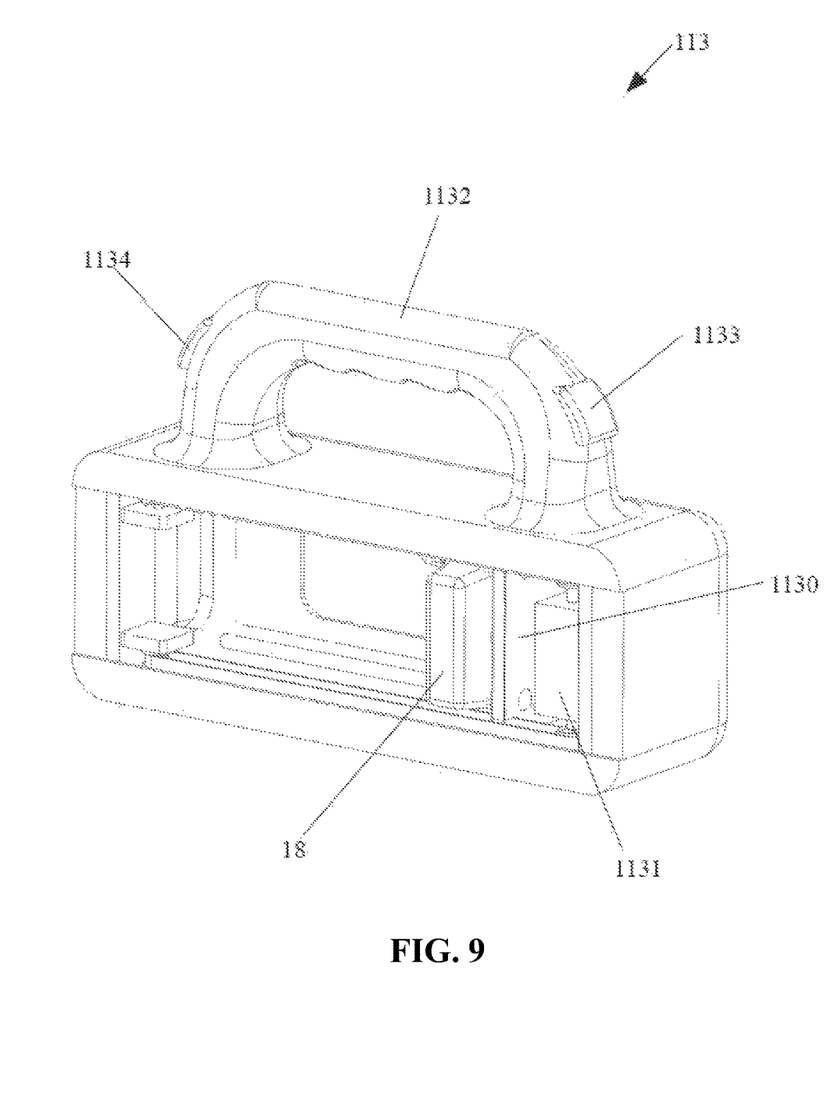
FIG. 9 is a schematic diagram illustrating a side scanning device of the embodiment.

As shown in FIG. 9, the mechanical driving system (11) further comprises a transverse movement drive (113). The transverse movement drive (113) comprises a transverse movement element (1130), and the transverse movement element (1130) is transversely movable. The whole breast ultrasound image-capturing device (1) yet further comprises a side scanning device (18), and the side scanning device (18) is mounted on the transverse movement drive (113).

In the present embodiment, the transverse movement drive (113) further comprises a step motor (1131), a pair of linear sliding rails, a timing belt, a handle (1132), a first button (1133), and a second button (1134). The transverse movement drive (113) can drive transverse movement of the side scanning device (18) for scanning. In one preferable embodiment, the transverse movement of the side scanning device (18) can achieve the scanning of the subject's accessory breasts. The handle (1132) is mounted on the transverse movement drive (113), and the two buttons (1133 and 1134) are mounted on two opposite sides of the handle (1132). With the first button (1133) and the second button (1134) pressed down, the side scanning device (18) is started to transversely move, and then the scanning image is gained. Since the first button (1133) and the second button (1134) are mounted on two opposite sides of the handle (1132), the user can easily operate the side scanning device (18) with a right hand or a left hand.

As above, the present invention reveals a simple-structured device to provide automatic ultrasound imaging techniques for whole breast. The device has powerful functions, and is light enough to be carried and transported.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A whole breast ultrasound image-capturing device, configured for breast scanning when a subject lies prone thereon, associated with an ultrasonic system when used, and comprising:
    an examination platform comprising an opening formed on a center of a top portion of the examination platform;
    a mechanical driving system mounted in the opening, and comprising:
        a frame mounted on a top portion of the mechanical driving system;
        a rotary module comprising a first gear, a second gear, and a drive motor, the first gear engaged with the second gear, and the drive motor connected to an axis of the first gear; and
        a radial movement drive comprising a translation mechanism, wherein the translation mechanism is radially movable;
    an array probe mounted in the radial movement drive;
    a probe holder connected to the translation mechanism to fix the array probe;
    a gel plate comprising a bottom portion connected to a cam surface of the second gear through multiple connecting frames, the gel plate mounted on a top portion of the probe holder, and the gel plate comprising a plate opening enclosing the array probe to expose the array probe out of the gel plate;
    a film assembly mounted in the frame, and the film assembly comprising:
        a film frame mounted in the frame; and
        a film mounted in the film frame;
    and the array probe emits ultrasound from a bottom thereof to penetrate the film so as to scan the breast.

2. The device as claimed in claim 1, wherein the mechanical driving system further comprises:
    a transverse movement drive comprising a transverse movement element; the transverse movement element is transversely movable.

3. The device as claimed in claim 2, further comprises:
    a side scanning device mounted on the transverse movement drive.

4. The device as claimed in claim 3, wherein the transverse movement drive further comprises a step motor, a pair of linear sliding rails, and a timing belt, so that the transverse movement drive drives transverse movement of the side scanning device for the scanning.

5. The device as claimed in claim 1, wherein a camera is mounted in front of the array probe.

6. The device as claimed in claim 5, wherein the camera is a charge-coupled device (CCD) camera or a complementary metal-oxide-semiconductor (CMOS) camera.

7. The device as claimed in claim 1, wherein the holder space is filled with a plastic crystal material.

8. The device as claimed in claim 7, wherein the plastic crystal material is alginate.

9. The device as claimed in claim 1, wherein the film is made of a biocompatible material.

10. The device as claimed in claim 1, wherein the film is made of a material selected from the group comprising polyethylene terephthalate (PET), polyethylene terephthalate glycol-modified (PETG), polyethylene, medical grade polyvinyl chloride (PVC), polycarbonate, polypropylene, polyether ether ketone (PEEK), and polyurethane.

* * * * *